(12) United States Patent
Khuri-Yakub et al.

(10) Patent No.: US 6,854,338 B2
(45) Date of Patent: *Feb. 15, 2005

(54) FLUIDIC DEVICE WITH INTEGRATED CAPACITIVE MICROMACHINED ULTRASONIC TRANSDUCERS

(75) Inventors: Butrus T. Khuri-Yakub, Palo Alto, CA (US); F. Levent Degertekin, Decatur, GA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/905,087

(22) Filed: Jul. 12, 2001

(65) Prior Publication Data

US 2002/0083771 A1 Jul. 4, 2002

Related U.S. Application Data

(60) Provisional application No. 60/218,940, filed on Jul. 14, 2000.

(51) Int. Cl.[7] ................................................. G01F 1/66
(52) U.S. Cl. ..................................... 73/861.27; 73/597
(58) Field of Search ........................ 73/861.27, 861.31, 73/861.26, 861.28, 861.29, 644, 642, 632, 599, 118.2; 347/54, 20, 68

(56) References Cited

U.S. PATENT DOCUMENTS

| | | | |
|---|---|---|---|
| 4,173,889 A | * 11/1979 | Forster et al. | ........... 73/861.27 |
| 4,484,478 A | * 11/1984 | Harkonen | ................ 73/861.25 |
| 5,606,351 A | * 2/1997 | Hawkins | ...................... 347/15 |
| 5,619,476 A | 4/1997 | Haller et al. | |
| 5,652,609 A | * 7/1997 | Scholler et al. | ................ 347/54 |
| 5,811,689 A | 9/1998 | Collier et al. | |
| 5,870,351 A | 2/1999 | Ladabaum et al. | |
| 5,894,452 A | 4/1999 | Ladabaum et al. | |
| 5,982,709 A | 11/1999 | Ladabaum et al. | |
| 6,004,832 A | 12/1999 | Haller et al. | |
| 6,070,468 A | 6/2000 | Degertekin et al. | |

OTHER PUBLICATIONS

Calmes, S., et al., "Highly Integrated 2–D Capacitive Micromachined Ultrasonic Transducers," *IEEE Ultrasonics Symposium*, 1999, 1163–1166.

* cited by examiner

*Primary Examiner*—Harshad Patel
(74) *Attorney, Agent, or Firm*—Dorsey & Whitney LLP

(57) ABSTRACT

The present invention provides fluidic devices and systems which have micromachined ultrasonic transducers integrated into microchannels. The ultrasonic transducers generate and receive ultrasonic waves. The transducers can be disposed and operated to measure fluid characteristics such as pressure, density, viscosity, flow rate and can also be used to mix and pump fluids.

24 Claims, 5 Drawing Sheets

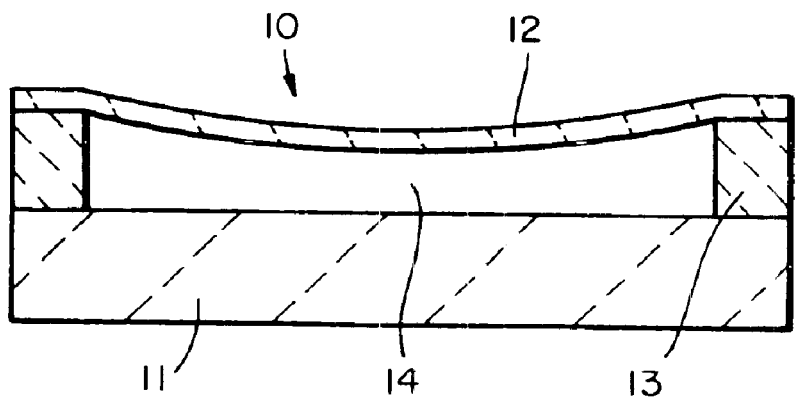
FIG_1
(PRIOR ART)
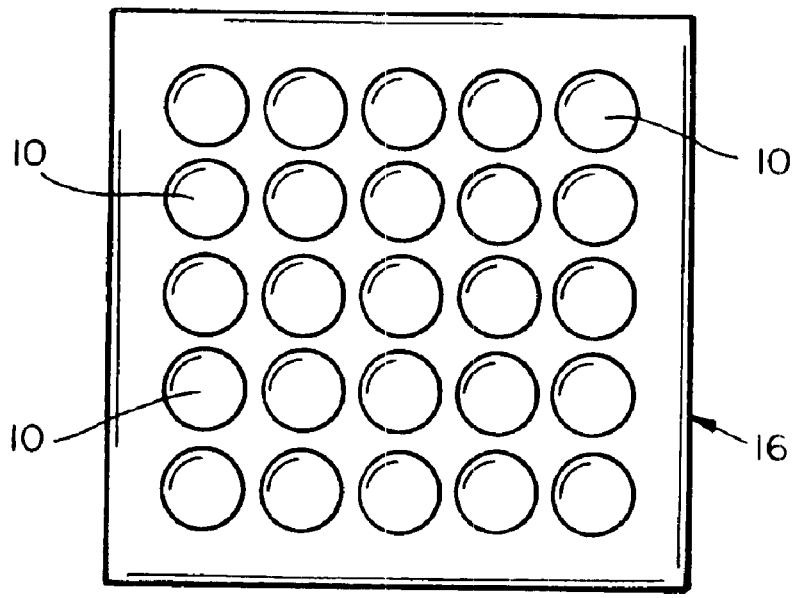
FIG_2
(PRIOR ART)

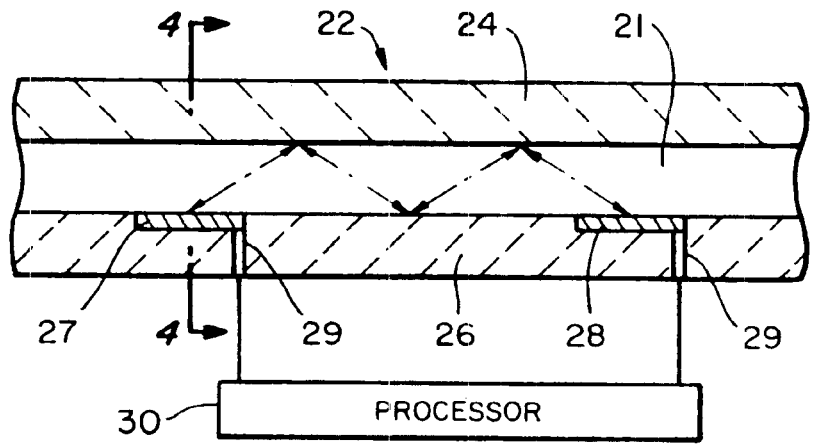
*FIG_3*
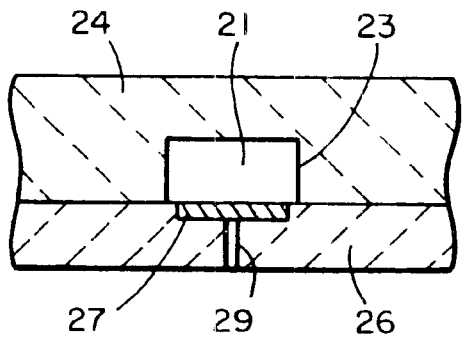
*FIG_4*
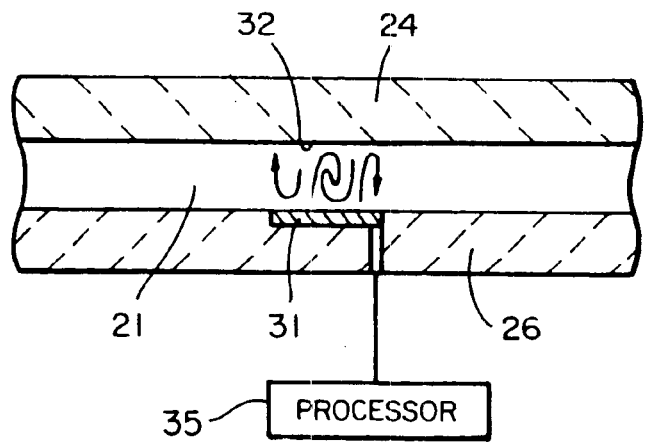
*FIG_5*

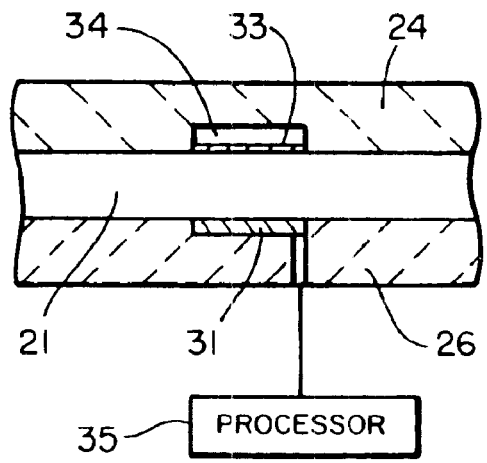
FIG_6
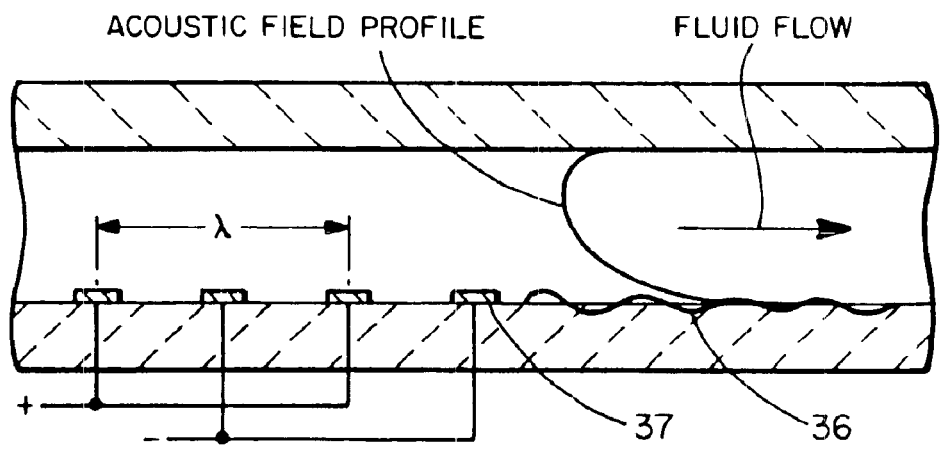
FIG_7
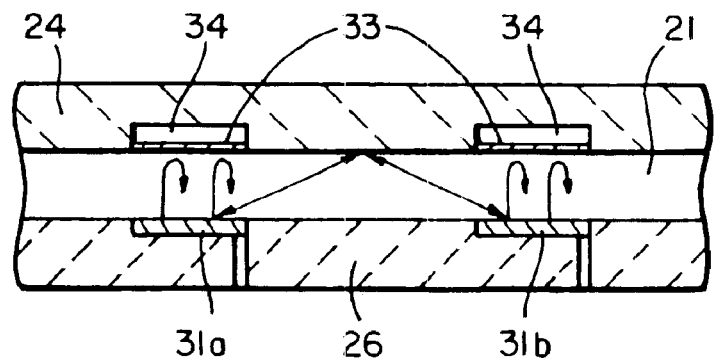
FIG_8

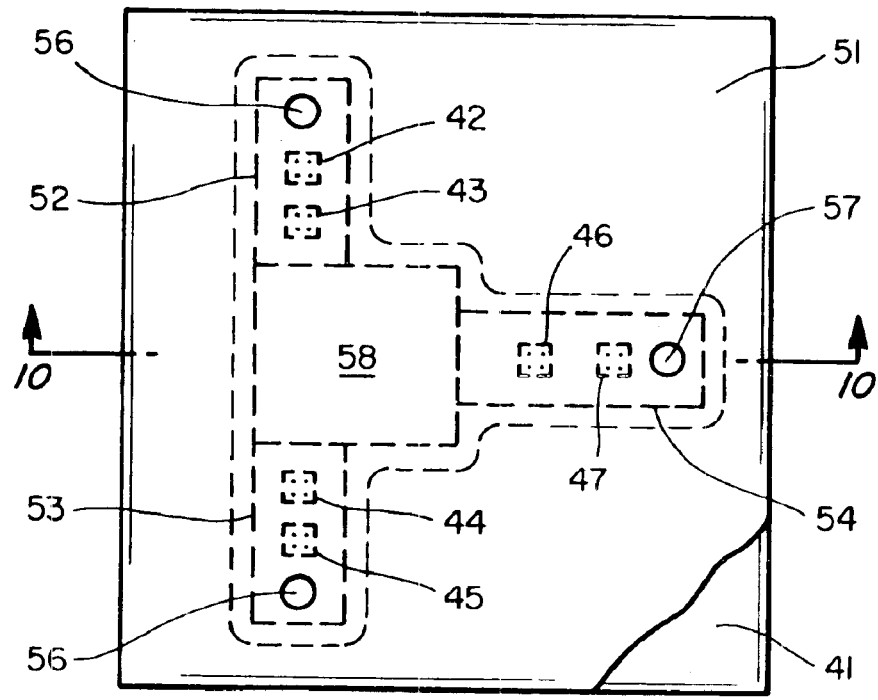
FIG_9
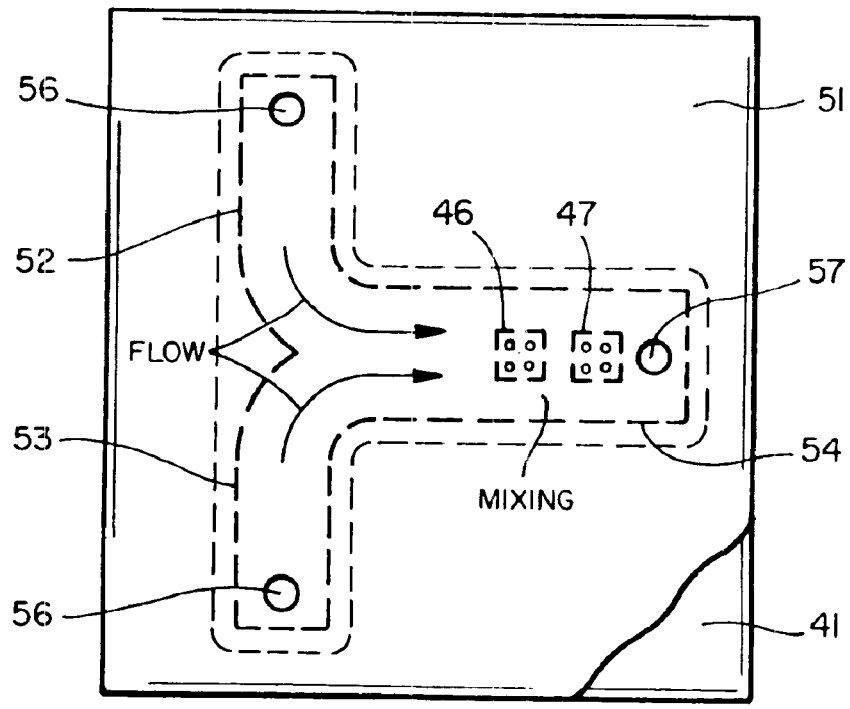
FIG_11

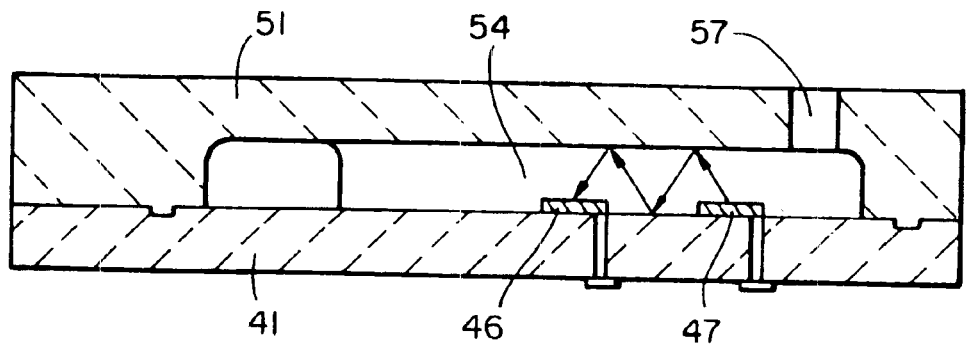
FIG_10
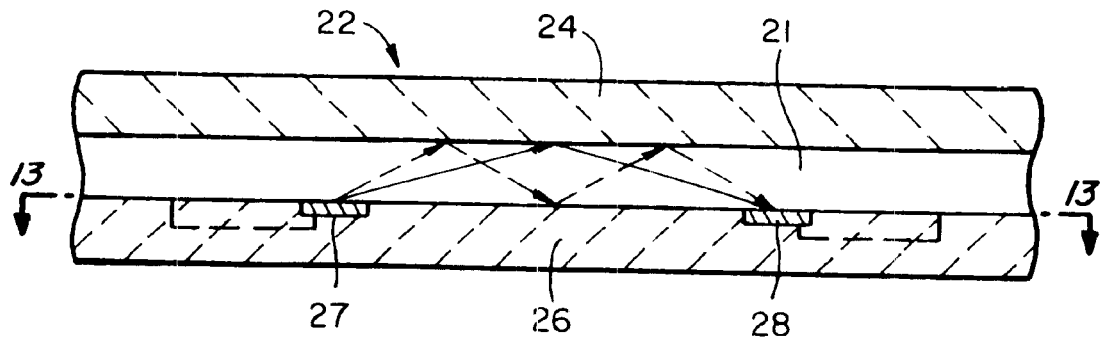
FIG_12
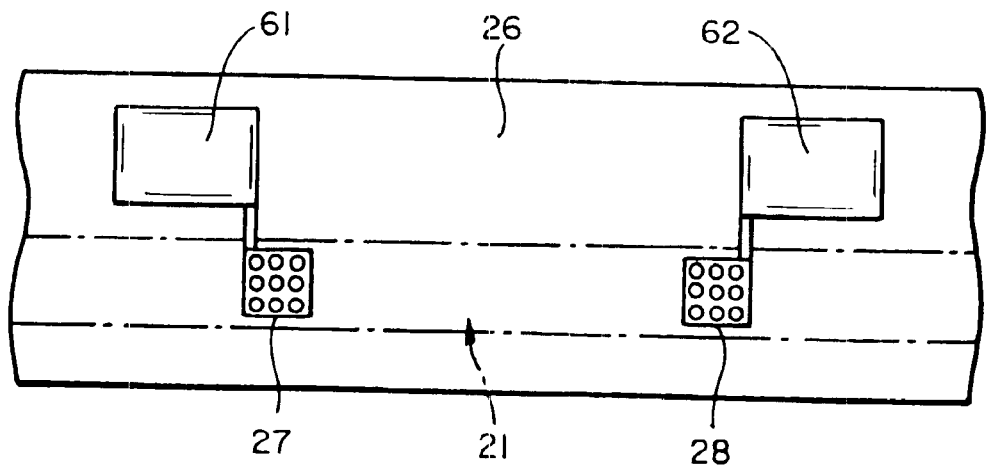
FIG_13

FLUIDIC DEVICE WITH INTEGRATED CAPACITIVE MICROMACHINED ULTRASONIC TRANSDUCERS

RELATED APPLICATIONS

This application claims priority to provisional application Ser. No. 60/218,940 filed Jul. 14, 2000.

BRIEF DESCRIPTION OF THE INVENTION

This invention relates to a fluidic device with integrated capacitive micromachined ultrasonic transducers (cMUTs), and more particularly to a fluidic device having microchannels with cMUTs fabricated in the walls of the channels.

BACKGROUND OF THE INVENTION

The large investments in the microelectronics industry converted integrated circuits laboratories into machine shops where miniature electromechanical systems are designed and built. Electromechanical as well as electro-optical systems have been miniaturized and used in many different applications. In the same fashion, miniaturization is presently applied in the field of microfluidics. Microfluidics technology provides the advantage of being able to perform chemical and biochemical reactions and/or separations with high throughput low volumes. Microfluidic systems employ microchannels in which chemical and biochemical materials are transported, mixed, separated and detected. The object is to take advantage of development in the silicon micromachining industry to develop laboratories on chips where fluids are manipulated, transported and tested. Electric and optical fields form the backbone of most of the methods used today in the transport and characterization of the fluids in channels.

Ultrasonic devices using piezoelectric materials have been successfully used for measurements of flow, physical properties and pressure of fluids and gases in many applications. Most of these devices are bulky, and they cannot be easily integrated to microfluidic systems for several reasons. With a few exceptions, piezoelectric materials are not compatible with other processing steps required for the fluidic chips. In addition, piezoelectric transducers for bulk wave excitation cannot be scaled down easily so as to fit in microfluidic channels without degrading their performance.

SUMMARY OF OBJECTS OF THE INVENTION

Using recent developments in the field of ultrasonic sensors and actuators they can be integrated into microfluidic channels. The integration of ultrasonic transducers in small channels will enable many applications that have heretofore been the domain of large scale ultrasonic sensors and actuators, micromachined ultrasonic transducers (cMUTs) integrated in channels will be used in applications such as. fluid pumping, measurements of pressure, density, viscosity, flow rate and other fluidic properties.

Capacitive micromachined ultrasonic transducers (cMUTs) operating both in air and water are know and described in U.S. Pat. Nos. 5,619,476, 5,870,351, 5,894,452. In both air and water, a Mason electrical equivalent circuit is used to represent the transducers and predict their behavior (W. P. Mason, *Electromechanical Transducers and Wave Filters* (Van Nostrand, N.Y., 1942)). These transducers are fabricated using standard IC processes and have been integrated with signal processing electronics to form an integrated system. In the article entitled "Highly Integrated 2-D Capacitive Micromachined Ultrasonic Transducers" appearing in IEEE Ultrasonic Symposium Proceedings pp. 1163–1666, 1999, S. Calmes et al. describe the fabrication of cMUTs with through wafer connections so that they can be flip-chip bonded to chips having signal processing electronics. The processing electronics can be implemented on the same silicon wafer avoiding the through wafer via structure. An example is provided in FIGS. 12 and 13. The dynamic range and bandwidth of cMUTs surpass their piezoelectric counterparts while being completely compatible with microfluidic chip fabrication processes.

cMUTs with dimensions of 100 $\mu$m or less are fabricated on the walls of the fluidic channels and operate in the 1-100 MHz frequency range. The cMUTs are surface micromachined to have a low surface profile, permitting undisturbed fluid flow. These transducers enable in-situ measurements of fluid flow, pressure, viscosity and temperature of the fluid in the channel. With their wide bandwidth, cMUTs can be used to implement resonators, time-of-flight measurements, and Doppler shift measurements in the fluid channel. It is also possible to excite traveling waves such as Stoneley waves at the fluid/channel wall interface to gently pump or mix fluids in the channel, in which case the cMUTs are used as actuators.

It is a general object of the present invention to provide fluidic channels having cMUTs fabricated in one wall of the channel for generating ultrasonic waves in said channel, and/or receiving ultrasonic waves.

BRIEF DESCRIPTION OF THE DRAWINGS

FIG. 1 is a schematic sectional diagram of a cMUT cell.

FIG. 2 is a plan view of a cMUT array with twenty-five cells.

FIG. 3 is a sectional view of a portion of a microfluidic channel including two cMUTs and signal processing electronics connected to the cMUTs by through wafer connections.

FIG. 4 is a sectional view of the channel of FIG. 3 taken along the line 4—4.

FIG. 5 is a sectional view of a portion of a microfluidic channel employing a single cMUT for determining acoustic impedance of fluid in the channel.

FIG. 6 is a sectional view of a portion of a microfluidic channel employing a single cMUT for determining fluid pressure.

FIG. 7 is a sectional view of a portion of a microfluidic channel employing a single cMUT employing interdigitated cMUTs for generating Stoneley waves.

FIG. 8 is a sectional view of a portion of a microfluidic channel employing two cMUTs for viscosity measurement.

FIG. 9 is a top plan view of a mixer employing microfluidic channels and cMUT sensors.

FIG. 10 is a sectional view taken along the line 10—10 of FIG. 9.

FIG. 11 is a plan view of mixer employing microfluidic channels and a cMUT mixer.

FIG. 12 is a sectional view of a microfluidic channel including two cMUTs and on-wafer signal processing electronics.

FIG. 13 is a sectional view taken along the line 13—13 of FIG. 12.

DESCRIPTION OF PREFERRED EMBODIMENTS

A cMUT cell is fabricated to form a structure similar to that of FIG. 1. The cell includes a substrate 11, such as silicon, and a membrane 12 such as silicon nitride supported by amorphous silicon 13. Amorphous silicon is used as a sacrificial layer that is partially removed by wet etching to form an evacuated cavity 14. A number of cells 10 are fabricated on a silicon substrate to form a transducer 16, FIG. 2. A detailed description of the methods for fabrication and operation of cMUTs is found in U.S. Pat. Nos. 5,619,476, 5,870,351 and 5,894,452, incorporated herein in their entirety. In the illustrated embodiment, the gap thickness is determined by the amorphous silicon and can be quite small, which results in improved sensitivity because in receive, one measures the change in capacity due to the motion of the membrane. Each cell is made of a vacuum-sealed, fully supported membrane with a diameter of 5-200 $\mu$m. For example, a 100 $\mu$m square transducer with individual cells 20 $\mu$m in diameter could be made with 25 such small membranes, FIG. 2.

In microfluidic technology, the chemical or biochemical reactions and/or separations take place in microchannels having dimensions in the range from 1 $\mu$m to 500 $\mu$m or more. Ultrasonic waves are ideal for measuring pressure, density, viscosity, flow rate and other properties of the fluids in the channels. Ultrasonic waves can also be used for fluid pumping. In accordance with the present invention, cMUTs are integrated into walls of the microchannels.

Referring to FIGS. 3 and 4, a microchannel 21 is shown in a section of a fluid conduit or capillary 22. The microchannel can for example have dimensions of 1 $\mu$m to 500 $\mu$m or more, dependent upon the application. The channel can be formed by micromachining a groove 23 in the top plate 24 and suitably sealing it to a bottom substrate 26. The top 24 can be glass, silicon or the like, into which the groove is machined, or it can be a polymeric material which can be machined or molded with the groove 23. In accordance with the present invention, the bottom substrate 26 is a semiconductor material such as silicon which is processed as described above to form integrated cMUTs such as cMUTs 27 and 28. The top surface of the cMUT is substantially coextensive with the bottom wall of the channel, thereby minimizing the influence of the cMUTs on the fluid flow. The cMUTs can be connected to known excitation and detector electronics or processor 30 using through-wafer vias 29 and flip-chip bonding techniques such as those described by Oralkan (O. Oralkan, X. C. Jin, F. L. Degertekin and B. T. Khuri-Yakub, "Simulation and experimental characterization of a 2-D cMUT array element", *IEEE Trans. UFFC*, 46,pp. 1337–40, 1999).

Using the configuration of cMUTs shown in FIGS. 3 and 4, the two cMUTs and the excitation and detection electronics are configured to alternately transmit and receive ultrasonic waves and to measure the times of flight of ultrasonic waves traveling along and opposite the direction of the flow. The difference in the time of flight in the two directions allows one to calculate the flow velocity of the fluid. With its wide bandwidth, the cMUT can easily separate ultrasonic pulses reflected up and down the fluidic channel. If the transmitting and receiving transducers are separated by 1 cm, and have the measurement ability to resolve 1/1000 of a period at 100 MHz, it is possible to measure a flow velocity of 1 mm/sec. Several different frequencies can be used to provide different path lengths to enhance the accuracy of the measurement as depicted in the same figure. As commonly used in medical imaging, Doppler methods can also be utilized for flow measurement in the channel.

Other important physical parameters of the fluid in the channel can also be obtained in-situ. A pulse-echo measurement off the opposite wall gives the speed of sound in the fluid which is a measure of its stiffness divided by the density. FIG. 5 is a sectional view showing a single cMUT 31 connected to a pulse echo processor 35. The processor excites the cMUT 31 which emits ultrasonic waves toward the opposite wall 32 and receiving the reflected waves. Multiple reflections between the walls of the channel can be used to set up resonance which can be used by the processor to determine the acoustic impedance, and hence the density and the viscosity of the fluid. The scattering from various structures in biological fluids, such as blood cells, can be detected using the cMUT in the pulse echo mode. This can be useful for both particle counting and Doppler shift.

The fluid pressure can be measured by a similar pulse-echo system monitoring the deformation of the channel. The fluid pressure will force the channel to deform in a predictable fashion, which in turn changes the path length of the reflected ultrasonic waves. In one embodiment, a compliant membrane 33 is fabricated on the wall opposite the cMUT, FIG. 6, with a vacuum-sealed gap 34 to reflect the ultrasonic wave in a pulse-echo measurement. The use of the vacuum-sealed gap will result in an absolute pressure measurement and a total reflection of the incident ultrasonic waves. The compliant membrane will have a large deflection for a given fluid pressure increasing the measurement sensitivity. For example, using a 0.4 $\mu$m thick 100 $\mu$m diameter silicon nitride membrane, deflections in the order of 1.5 Å will be obtained for 1 Pa of fluid pressure. Using an ultrasonic time-of-flight (TOF) measurement with 1 ps resolution (off the shelf equipment can measure TOF down to 0.25 ps), one should obtain a pressure resolution of 5 Pa, assuming all other parameters, such as temperature, are calibrated out. As will be discussed later, an array of these compliant membranes and corresponding cMUTs can be placed along the channel to monitor the pressure drop due to the fluid flow and measure the fluidic resistance of the channel.

Since the dimensions of individual membranes forming the cMUTs are much smaller than the wavelength of the sound waves in the fluid, cMUTs generate significate evanescent fields in the fluid. In addition, at the edges, where the membranes are connect to the substrate, the motion of the cMUT membrane is coupled to the substrate. This combination n results in an efficient excitation of propagating Stoneley waves at the fluid/substrate interface as shown in FIG. 7. Stoneley waves have an elliptical particle velocity field in the fluid that decays along the thickness of the channel. Hence, it is possible to move the fluid along the shallow channel by the traveling Stoneley waves which effectively turn the bottom surface of the chann el into a distributed pump.

One can selectively excite Stoneley waves 36 while not coupling into the bulk waves in the channel by fabricating interdigitated cMUTs 37 on the wall of the fluidic channel as shown in FIG. 7. The mode selectivity is achieved by matching the spatial period of the cMUTs to the wavelength of the desired propagation mode. By applying in and out of phase signals to consecutive fingers, bulk wave radiation to the fluid can be avoided. By employing three spaced fingers or electrodes and applying 120° phase shifted signals, unidirectional fluid flow can be obtained. The traveling acoustic field in the channel has elliptical particle displacement fields that decay in the distance of $\lambda/2\pi$ from the excitation transducer surface, where $\lambda$ is the wavelength of acoustic waves as shown in FIG. 7. For a water-like fluid, this will be around 24 $\mu$m for Stoneley waves at 100 MHz. Hence, this frequency would be suitable for a typical channel height of 30 $\mu$m. At lower frequencies, the Stoneley wave will also couple to the top surface of the channel to generate plane wave-like modes traveling along the length of the channel. These modes will be useful in determining the flow rate of the fluid.

The Stoneley wave mode is evanescent in the case of a fluid/half-space structure and it will inherently provide more robust and repeatable sensors and actuators. These evanescent propagation modes will find many applications in measuring the properties of fluid and gas medium which flow in the microchannels.

Since the Stoneley waves are evanescent in the fluid, they propagate without damping if there is no loss in the fluid or solid substrate material. In a real fluid, the attenuation of these waves will be determined by the viscosity of the fluid. Hence, one can measure the fluid viscosity in a microfluidic channel by monitoring the amplitude of the Stoneley waves propagating a known distance in the channel. It has been shown that, for Lamb waves in thin plates, the insertion loss along a propagation path in dB is a linear function of fluid viscosity.

Another approach for viscosity measurement depends on the measurement of the fluidic resistance of the channel. The fluidic resistance of a channel with a rectangular cross-section and a length L is given by $$R = \frac{\Delta P}{Q} = \frac{12\eta L}{wh^3}$$

where $\Delta P$ is the pressure drop in the channel in Pa, Q is the volume flow rate in $m^3/s$, w is the width, h is the height of the channel, and $\eta$ is the viscosity of the fluid. Given the flow rate of the fluid and the pressure drop in the channel for a given length L, one can find the viscosity of the fluid for a given channel geometry. Combining the ultrasonic flow measurement with the pressure drop measured using an array of pressure sensors 31a and 3b as shown in FIG. 8, the viscosity can be monitored accurately. We note that the fluidic resistance expression is valid for a large w/h ratio, which would be valid in most cases. For microfluidic channels, the flow resistance, hence the pressure drops, may be significant even for small flow rates due to small dimensions. For example, for a 1 mm long water flow channel with 100 $\mu$m width and 30 $\mu$m height, the pressure drop will be (R=8×10$^{12}$)133 Pa (~18 Torr) for 1 $\mu$l/min flow rate. If the pressure differences down to 5 Pa can be measured using the ultrasonic pulse-echo method, then a viscosity resolution of 0.07 centipoise can be achieved.

An example of the integration of cMUTs in the microchannels of a microfluidic device for fluid mixing and/or reaction is illustrated in FIGS. 9 and 10. The device includes a planar base 41 with integrated pairs of cMUTs 42 and 43, 44 and 45, and 46 and 47. Through wafer vias will carry electrical signals to the cMUTs. The pairs of cMUTs may be configured to generate Stoneley waves which would pump the fluid in the channels, or configured to measure the flow, or operated individually to sense pressure or other characteristics of the fluid in the channel. It is of course apparent that more cMUTs may be integrated to carry out the measurements discussed above.

In this example, a top glass wafer 51 is wet-etched to form input channels 52 and 53 and output channel 54. Fluid inlet and outlet ports 56 and 57 extend through the glass wafer to communicate with the channels. The glass wafer is suitably bonded to the planar base to form the microchannels over the cMUTs. The fluid flow through the input channels to the mixing chamber 58 and the reacted or mixed fluid flows through the outlet channel.

FIG. 11 shows another embodiment of a fluid mixer. In this embodiment, the channels 52 and 53, FIG. 9, merge smoothly into the channel 54. Parts in FIG. 11 bear like reference numbers for like parts in FIG. 9. The fluid which flows laminarly in the channels 52 and 53 travels as separate streams in the channel 54 and is mixed by action of one or both cMUTs 46 and 47.

As referred to above, the signal processing electronics can be connected to the cMUTs and carried on the surface of the wafer. FIGS. 12 and 13 show cMUTs 27 and 28 as in FIGS. 3 and 4 mounted in a microchannel 21. Signal processing and excitation integrated circuits 61 and 62 are mounted in the surface of the wafer 26 and connected along the surface of the wafer to the cMUTs rather than through vias.

The in-situ fluidic sensing and actuation schemes proposed for microfluidic channels enjoy the same advantages which has made the conventional, large-scale ultrasonic devices the popular choice for fluid measurements in industry. The high frequency cMUTs enable implementation of these techniques in microfluidic applications.

Especially in biological applications, it is critical to have fluidic sensors which do not interfere with the flow or affect the properties of the fluid. The microfluidic flow sensors based on dilution measurement of thermal, optical or ionic tracers require injection of heat, charge or light into the flow channel. Some other techniques measure the drag force exerted on some specific structures inserted in the flow channel. Examples of these include capacitive or piezo-resistive measurement of the deflection of a cantilever placed in the flow channel. In most cases, these structures have to be fabricated separately and the flow channel is modified to fit the sensing structure disturbing the regular flow pattern. In contrast, the cMUTs are surface micromachined to have a very low vertical profile and they will be an integral part of the channel wall. The ultrasonic sensors used for flow measurement do not require any thermal cycles or injection of tracers in the fluid flow, hence it is a non-intrusive technique.

Ultrasonic fluid pumping has inherent advantages due to its distributed-drive mechanism as compared to the scaled down discrete pumps which require a drastic increase in the number of pumping stations and strength to keep up with the increased flow resistance in microfluidic channels. The cMUTs can operate at fairly low voltages to generate ultrasonic waves as compared to the pumps with direct electrostatic actuation. The fabrication of cMUTs are simple, all the micromachining is performed on a single wafer using the standard semiconductor manufacturing techniques as opposed to electrostatically or magnetically actuated pumps with many hand-assembled moving parts. Also, the pumping is gentle; there are no thermal cycles or valve closures that could damage fragile biomolecules such as DNA. Furthermore, there are no restrictions on the type of fluid which may be pumped using ultrasonic pumps. For example, hydrodynamic pumps cannot be used to pump conductive fluids.

The foregoing descriptions of specific embodiments of the present invention are presented for the purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that

What is claimed is.

1. A fluidic device comprising.
   at least one microchannel, and
   at least one capacitive micromachined ultrasonic transducer formed in one wall of said microchannel.

2. A fluidic device as in claim 1 in which the microchannel dimensions in the range 1 $\mu$m to 500 $\mu$m or more.

3. A fluidic device comprising:
   a base of semiconductor material,
   at least one capacitive micromachined ultrasonic transducer formed in said base of semiconductor material, and
   a top having a microgroove sealed to said base with the microgroove over the ultrasonic transducer whereby to form a microchannel with an ultrasonic transducer in on wall of said channel.

4. A fluidic device as in claim 3 in which the microchannel has dimensions in the range of 1–500 $\mu$m.

5. A fluidic device as in claim 4 including at least two longitudinally spaced transducers and said top has its microgroove oriented both of said transducers.

6. A fluidic device as in claim 5 including a process for operating said ultrasonic transducers to measure the time-of-flight of ultrasound in the direction and the opposite direction of fluid flow and provide a measure of fluid velocity.

7. A fluidic device as in claim 5 including a processor for driving said ultrasonic transducers to generate Stoneley waves for pumping fluid in said channels.

8. A fluidic device as in claim 4 in which said microgroove includes a compliant membrane which is disposed opposite said ultrasonic transducer.

9. A fluidic device as in claim 8 in which a processor operates said transducer to generate ultrasonic pulses which are reflected by said membrane and processes the pulse and echo signal to measure the pressure of the fluid in said microchannel.

10. A fluidic device as in claim 9 including a plurality of ultrasonic transducers and membranes spaced along the channel to thereby measure the pressure drop along the channel.

11. A fluidic device as in claim 4 including a processor for said ultrasonic transducer to emit pulses which echo off the opposite wall and process the pulse and echo signals to provide a measure of the acoustic impedance of the fluid in said microchannel.

12. A flexible device as in claim 11 including a processor configured to process signals to and from said ultrasonic transducer and providing an output indicative of pressure.

13. A fluidic device as in claim 4 including a processor for operating said ultrasonic transducer to emit pulses and set ultrasonic resonance whereby to measure fluid properties or for counting particles in said fluid.

14. A fluidic device as in claim 4 in which the base is silicon or a dielectric material.

15. A fluidic device as in claim 4 in which the micromachined ultrasonic transducer is operated to mix fluids in the channel.

16. A fluidic device comprising.
    at least one microchannel having opposed walls,
    at least one capacitive micromachined ultrasonic transducer micromachined into one wall, and
    a flexible membrane on the opposite wall opposite the ultrasonic transducer whereby ultrasonic waves from the ultrasonic transducer are reflected back to the transducer by the flexible membrane.

17. A fluidic device comprising.
    a silicon base,
    one or more capacitive micromachined ultrasonic transducers formed into said base, and
    a top having a microgroove sealed to said base with the microgroove over said capacitive micromachined ultrasonic transducers.

18. A fluidic device as in claim 17 including at least two capacitive micromachined transducers spaced along said channel.

19. A fluidic device as in claim 17 including a processor for operating said transducers in a pulse echo mode.

20. A fluidic device as in claim 18 including a processor for operating said transducers to receive ultrasonic pulses from one another.

21. A fluidic device as in claim 19 in which said microgroove includes a compliant membrane opposite said ultrasonic transducer.

22. A fluidic device as in claim 18, including a processor for operating the micromachined ultrasonic transducer to mix fluids in the channel.

23. A fluidic device as in claim 17 in which the ultrasonic transducer is operated to pump fluids in said channel.

24. A fluidic device as in claim 17 in which said ultrasonic transducer is operated to measure fluid characteristics.

* * * * *